US009155753B2

(12) United States Patent
Tressler et al.

(10) Patent No.: US 9,155,753 B2
(45) Date of Patent: Oct. 13, 2015

(54) TREATMENT OF CARCINOMAS WITH A COMBINATION OF EGF-PATHWAY AND TELOMERASE INHIBITORS

(75) Inventors: Robert J. Tressler, Capitola, CA (US); Ning F. Go, Palo Alto, CA (US)

(73) Assignee: Geron Corporation, Menlo Park, CA (US)

( * ) Notice: Subject to any disclaimer, the term of this patent is extended or adjusted under 35 U.S.C. 154(b) by 765 days.

(21) Appl. No.: 12/530,014

(22) PCT Filed: Mar. 6, 2008

(86) PCT No.: PCT/US2008/003001
§ 371 (c)(1),
(2), (4) Date: Nov. 30, 2009

(87) PCT Pub. No.: WO2008/112129
PCT Pub. Date: Sep. 18, 2008

(65) Prior Publication Data
US 2010/0104586 A1    Apr. 29, 2010

Related U.S. Application Data

(60) Provisional application No. 60/905,944, filed on Mar. 9, 2007.

(51) Int. Cl.
*A61K 31/7088*    (2006.01)
*A61K 39/395*    (2006.01)
*A61K 45/06*    (2006.01)

(52) U.S. Cl.
CPC ....... *A61K 31/7088* (2013.01); *A61K 39/39558* (2013.01); *A61K 45/06* (2013.01)

(58) Field of Classification Search
CPC ............... A61K 51/1051; A61K 47/48584; A61K 51/1054; A61K 47/48592
See application file for complete search history.

(56) References Cited

U.S. PATENT DOCUMENTS

| | | | |
|---|---|---|---|
| 4,394,448 A | 7/1983 | Szoka, Jr. et al. | |
| 4,897,355 A | 1/1990 | Eppstein et al. | |
| 5,583,016 A | 12/1996 | Villeponteau et al. | |
| 5,656,638 A | 8/1997 | Gaeta et al. | |
| 5,695,932 A | 12/1997 | West et al. | |
| 5,760,062 A | 6/1998 | Gaeta et al. | |
| 5,767,278 A | 6/1998 | Gaeta et al. | |
| 5,770,613 A | 6/1998 | Gaeta et al. | |
| 5,863,936 A | 1/1999 | Gaeta et al. | |
| 5,952,490 A | 9/1999 | Hanecak et al. | |
| 6,261,836 B1 | 7/2001 | Cech et al. | |
| 6,331,399 B1 | 12/2001 | Monia et al. | |
| 6,368,789 B1 | 4/2002 | West et al. | |
| 6,444,650 B1 | 9/2002 | Cech et al. | |
| 6,852,318 B1 * | 2/2005 | Varner | 424/130.1 |
| 6,887,873 B2 * | 5/2005 | Mailliet et al. | 514/245 |
| 7,067,497 B2 | 6/2006 | Hanecak et al. | |
| 7,494,982 B2 | 2/2009 | Gryaznov et al. | |
| 2004/0197328 A1 * | 10/2004 | Young et al. | 424/141.1 |
| 2005/0113325 A1 | 5/2005 | Gryaznov et al. | |
| 2006/0009636 A1 | 1/2006 | Gryaznov et al. | |
| 2007/0015723 A1 | 1/2007 | Hanecak et al. | |
| 2007/0015837 A1 | 1/2007 | Kun et al. | |
| 2007/0270363 A1 | 11/2007 | Bennett et al. | |
| 2010/0010064 A1 | 1/2010 | Moore et al. | |
| 2010/0016407 A1 | 1/2010 | Go et al. | |
| 2010/0113571 A1 | 5/2010 | Gryaznov et al. | |

FOREIGN PATENT DOCUMENTS

| | | | |
|---|---|---|---|
| WO | WO-89/06692 | 7/1989 | |
| WO | WO-98/28442 | 7/1998 | |
| WO | WO 03/070234 A1 * | 8/2003 | ............. A61K 31/13 |
| WO | WO-2005/023994 | 3/2005 | |
| WO | WO-2006/113426 | 10/2006 | |
| WO | WO-2006/113470 | 10/2006 | |
| WO | WO-2006/124904 | 11/2006 | |
| WO | WO-2008/054711 | 5/2008 | |
| WO | WO-2008/094640 | 8/2008 | |

OTHER PUBLICATIONS

Pegram et al. (Oncogene 1999 18: 2241-2251).*
Dillman (Annals of Internal Medicine, 1989 111:592-603).*
ATCC CCL-185TM (M. Lieber Mar. 2009).*
Wiesenthal (http://weisenthal.org/feedback. html, Feb. 4, 2002).*
Berenbaum (Clin. Exp Immunol. 28:1-18, 1977).*
NCI Drug Dictionary-National Cancer Institute (trastuzumab, http://www.cancer.gov/drugdictionary?cdrid=42265, downloaded Aug. 6, 2014).*
Dikmen et al. (Cancer Res. Sep. 1, 2005 65(17) 7866-7873).*
Humblet et al. (Expert Opin. Pharmacother. 2004 5(7): 1622-1633).*
Supplementary European Search Report for EP 08726518.7, mailed Oct. 5, 2010, 3 pages.
PCT Search Report for PCT/US20081003001, mailed Sep. 5, 2008, 1 page.
Stratagene Catalog (1988), p. 39.
Asai, A. et al., "A Novel Telomerase Template Antagonist (GRN163) as a Potential Anticancer Agent", *Cancer Res. 63* 2003), pp. 3931-3939.
Blackburn E., "Telomerases" *Annu. Rev Biochem.* 61 pp. 113-129.
Chen, J. et al., "Secondary structure of vertebrate telomerase RNA". *Cell 100*(2000), pp. 503-514.
Fendly, B. et al, "Characterization of murine monoclonal antibodies reactive to either the human epidermal growth factor receptor or HER2/neu gene product", *Cancer Res.* 50 (1990), pp. 1550-1558.
Go, N. et al., "Single agent and combination treatment studies with the telomerase inhibitor GRN163L in ovarian cancer and non-small cell lung carcinoma (NSCLC) xenograft models", *Eur. J. Cancer* 4(Suppl. 12) (2006), p. 189, Abstract.

(Continued)

Primary Examiner — Peter J Reddig
(74) *Attorney, Agent, or Firm* — Carol L. Francis; Glenn J. Foulds; Bozicevic, Field & Francis LLP

(57) ABSTRACT

A method and kit for inhibiting the proliferation of carcinoma cells are disclosed, based on a combination of an EGF pathway inhibitor and a telomerase inhibitor. When used in cancer therapy, the two compounds in combination enhance the anticancer treatment efficacy obtained with the antibody alone or the telomerase inhibitor alone.

12 Claims, 3 Drawing Sheets

(56) References Cited

OTHER PUBLICATIONS

Goldblatt, E. et al., "Lipid-conjugated telomerase template antagonists sensitize resistant HER2-positive breast cancer cells to trastuzumab", *Breast Cancer Res. Treat.* 118(1) (2009), pp. 21-32.

Gowan, S. et al., "A G-quadruplex-interactive potent small-molecule inhibitor of telomerase exhibiting in vitro and in vivo antitumor activity", *Mol. Pharmacol.* 61(5) (2002), pp. 1154-1162.

Gryaznov, S. et al., "Oligonucleotide N3'->P5' thiophosphoramidate telomerase template antagonists as potential anticancer agents", *Nucleosides, Nucleotides & Nucl. Acids* 22(5-8) (2003), pp. 577-581.

Harley, C. ,"Telomere loss: Mitotic clock or genetic timebomb?", *Mutation Res.* 256 (1991), pp. 271-282.

Herbert, B-S. et al., "Lipid modfrication of GRN163, an N3'-P5' thio-phosphoramidate oligonucleotide, enhance the potency of telomerase inhibition", *Oncogene* 24 (2005), pp. 5262-5268.

Herbert, B-S. et al., "Oligonucleotide N3'->P5' phosphoramidates as efficient telomerase inhibitors", *Oncogene* 21(4) (2002), pp. 638-642.

Hochreiter, A. et al., "Telomerase template antagonist GRN163L disrupts telomere maintenance, tumor growth, and metastasis of breast cancer", *Clin. Cancer Res.* 12(10) (2006), pp. 3184-3192.

Hudziak, R. et al., "p185HER2 monoclonal antibody has antiproliferative effects in vitro and sensitizes human breast tumor cells to tumor necrosis factor", *Mol. Cell. Biol.* 9 (1989), pp. 1165-1172.

Kim, M. et al., "A low threshold level of expression of mutant-template telomerase RNA inhibits human tumor cell proliferation", *Proc. Natl. Acad. Sci. USA* 98(14) (2001), pp. 7982-7987.

Kraemer, K. et al., "Chemosensitization of bladder cancer cell lines by human telomerase reverse transcriptase antisense treatment", *J. Urology* 172(5 Pt. 1) (2004), pp. 2023-2028.

Kupihar, Z. et al., "Synthesis and application of a novel, crystalline phosphoramidite monomer with thiol terminus, suitable for the synthesis of DNA conjugates", *Bioorg. Med. Chem.* 9(5) (2001), pp. 1241-1247.

Lebedeva, I. et al., "Antisense oligonucleotides: promise and reality", *Annu. Rev. Pharmacol. Toxicol.* 41 (2001), pp. 403-419.

Lupu, R. et al., "Direct interaction of a ligand for the erbB2 oncogene product with the EGF receptor and p185erbB2", *Science* 249 (1990), pp. 1552-1555.

Macejak, D et al., "Adenovirus-mediated expression of a ribozyme to c-myb mRNA inhibits smooth muscle cell proliferation and neointima formation in vivo", *J. Virol.* 73(9) (1999), pp. 7745-7751.

McCurdy, S. et al., "An improved Method for the Synthesis of N3'->P5' Phosphoramidate Oligonucleotides", *Tetrahedron Lett.* 38(2) (1997), pp. 207-210.

Mishra, R. et al., "Improved leishmanicidal effect of phosphorotioate antisense oligonucleotides by LDL-mediated delivery", *Biochem. Biophys. Acta* 1264(2) (1995), pp. 229-237.

Nahta, R. et al., "Mechanism of disease: understanding resistance to HER2-targeted therapy in human breast cancer", *Nature Clin. Practice Oncol.* 3 (2006), pp. 269-280.

Nelson, J. et al., "N3'-P5' oligodeoxyribonucleotide phosphoramidates: a new method of synthesis based on a phosphoramidate amine-exchange reaction", *J. Org. Chem.* 62 (1997), pp. 7278-7287.

Pascolo, E. et al., "Mechanism of human telomerase inhibition by BIBR1532, a synthetic, non-nucleosidic drug candidate", *J. Biol. Chem.* 277(18) (2002), pp. 15566-15572.

Pongracz, K. et al., "Oligonucleotide N3'→P5' thiophosphoramidates: synthesis and properties", *Tetrahedron Lett.* 49 (1999), pp. 7661-7664.

Pruzan, R. et al., "Allosteric inhibitors of telomerase: oligonucleotide N3'->P5' phosoramidates", *Nucl. Acid Res.* 30(2) (2002), pp. 559-568.

Rump, E. et al., "Preparation of conjugates of oligodeoxynucleotides and lipid structures and their interaction with low-density lipoprotein", *Bioconjugate Chem.* 9 (1998), pp. 341-349.

Shea, R. et al., "Synthesis, hybridization properties and antiviral activity of lipid-oligodeoxynucleotide conjugates", *Nucl. Acids Res.* 18(13) (1990), pp. 3777-3783.

Shepard, H. et al., "Resistance of tumor cells to tumor necrosis factor", *Clin. Immunol.* 8 (1988), pp. 333-395.

Uhlmann, E. et al., "Antisense oligonucleotides: a new therapeutic principle", *Chem. Rev.* 90 (1990) pp. 543-584.

Ward, R. et al., "Pharmacological telomerase inhibition can sensitize drug-resistant and drug-sensitive cells to chemotherapeutic treatment", *Mol. Pharmacol.* 68 (2005), pp. 779-786.

Zeng, Y. et al., "MicroRNAs and small interfering RNAs can inhibit mRNA expression by similar mechanisms", *Proc. Natl. Acad. Sci. USA* 100(17) (2003), pp. 9779-9784.

\* cited by examiner

TREATMENT OF CARCINOMAS WITH A COMBINATION OF EGF-PATHWAY AND TELOMERASE INHIBITORS

CROSS REFERENCE TO RELATED APPLICATIONS

This application is a U.S. National Phase application of PCT/US2008/003001, filed Mar. 6, 2008, which claims priority to U.S. Provisional Appl. No. 60/905,944, filed Mar. 9, 2007, both of which are incorporated by reference in their entirety.

REFERENCE TO A SEQUENCE LISTING

A Sequence Listing was filed electronically for this application as an ASCII text file, named Seqlist.txt, created on Sep. 29, 2009 and containing 5,853 bytes. This Sequence Listing is hereby incorporated in its entirety by reference into the specification.

FIELD OF THE INVENTION

The invention is directed to treatment of carcinomas by a combination of an EGF pathway inhibitor, such as an anti-EGF receptor antibody, and a telomerase inhibitor.

BACKGROUND

In view of the continuing high number of deaths each year resulting from cancer, a continuing need exists to identify effective and less toxic therapeutic regimens for use in anti-cancer treatment.

For a variety of epithelial cell cancers, or carcinomas, treatment with an epithelial growth factor (EGF) pathway inhibitor has been proposed or demonstrated. Trastuzumab (Herceptin®), a humanized monoclonal that specifically targets the human epidermal growth factor 2 (HER2) receptor, inhibits the EGF signaling pathway associated with HER2. The anti-HER2 antibody may be indicated particularly in the treatment of cancers, such as breast and ovarian cancers, characterized by HER2 overexpression in carcinoma cells.

Cetuximab (Erbitux®) is a chimeric monoclonal antibody that likewise acts as an EGF pathway inhibitors by binding to epidermal growth factor receptor 1 (EGFR, ErbB-1 or HER1), and may be indicated, for example, for the treatment of metastatic colorectal cancer and head and neck cancer.

A number of small molecule anti-cancer agents that target the EGF pathway have also been proposed in anti-cancer treatment. Erlotinib (Tarceva®) and gefitinib (Iressa®) specifically target the tyrosine kinase activity of EGFR, which may be highly expressed and occasionally mutated in various forms of cancer. The drug molecules bind in a reversible fashion to the adenosine triphosphate (ATP) binding site of the receptor, effectively blocking autophosphorylation of EGFR homodimers, and thus blocking the signal cascade to the nucleus. Both compounds have shown a survival benefit in the treatment of lung cancer in phase III trials, and have been approved for the treatment of locally advanced or metastatic non small cell lung cancer.

EGF pathway inhibitors are but one class of a large number of anti-cancer agents that may be selected for treating cancer. In addition, any selected class of anti-cancer agent may be tested with one or more other anti-cancer agents in a combination treatment, to determine if the two or more agents together are capable of producing an additive therapeutic effect, or other significant advantage, such as a reduction in undesired side effects, due to a reduced dose of the more toxic component, and/or a reduction in the development of drug-resistance in the cancer being treated.

It would be desirable to provide a combined-drug cancer therapy for the treatment carcinomas in which both drug components are relatively specific against cancer cells, each acting through a mechanism that involves specific binding of the drug compound to a cellular component associated preferentially with the cancer cells.

SUMMARY OF THE INVENTION

The invention includes a method for inhibiting the proliferation of carcinoma cells that express an EGF receptor, by (a) exposing the cells to an EGF pathway inhibitor, such as an anti-EGF-receptor antibody, and (b) either proceeding, following, or concomitantly with step (a), exposing the cells to a telomerase inhibitor. In one embodiment, the amount of antibody to which the cells are exposed is effective, by itself, to inhibit proliferation of the cancer cells. In a further embodiment, the amount of both antibody and inhibitor is effective, by itself, to inhibit proliferation of the cancer cells. The combination may provide an enhanced cancer-cell inhibiting effect with respect to either component alone.

The telomerase inhibitor may include an oligonucleotide having nuclease-resistant intersubunit linkages and an oligonucleotide sequence effective to bind by sequence-specific hybridization to a template region of hTR. The internucleoside linkages in the oligonucleotide may be selected from N3'→P5' phosphoramidate and N3'→P5' thiophosphoramidate linkages. The telomerase inhibitor may include a lipid moiety, such as a fatty acid, sterol, or derivative thereof, which is attached covalently at one end of the oligonucleotide. The oligonucleotide may be 10-20 bases in length, preferably 13-20 bases in length, and may have the sequence identified by SEQ ID NO:12 (5'-TAGGGTTAGACAA-3'). One exemplary telomerase inhibitor is the compound designated herein as GRN163L.

The method may be used in treating a subject having a carcinoma, and in exemplary embodiments, for treating a subject having breast or ovarian cancer characterized by elevated levels of HER2 on the surface of the cancer cells, where exposing step (a) includes administering the anti-EGF receptor antibody to the subject in an amount effective, when administered alone, to inhibit proliferation of cancer cells in the subject. Prior to treatment, the subject may be confirmed to have elevated levels of EGF receptor, such as HER2, associated with the cancer cells.

In a further embodiment, each exposing step (a) and (b) includes administering the EGF pathway inhibitor and telomerase inhibitor to the subject in an amount effective, when administered alone, to inhibit proliferation of cancer cells in the subject. Where the telomerase inhibitor is the compound GRN163L, it may be administered to the subject by intravenous infusion, under infusion conditions effective to produce a blood concentration of the inhibitor of between 1 nM and 100 uM. The antibody may also be administered to the subject in by infusion, at a dose effective to produce a blood concentration of the antibody between about 25-500 microgram/ml.

In another aspect, the invention is directed to a method for enhancing the efficacy of an EGF pathway inhibitor in the treatment of a carcinoma, and in exemplary embodiments, enhancing the efficacy of an anti-EGF receptor antibodies, such as anti-HER2 antibody, in the treatment of a carcinoma, and in exemplary embodiments, carcinomas such as breast, ovarian cancer or non-small-cell lung carcinomas, having elevated levels of expressed HER2. The method includes administering to the subject, before, during, or after administering an EGF pathway inhibitor, an oligonucleotide telomerase inhibitor of the type composed of an oligonucleotide having nuclease-resistant intersubunit linkages and an oligonucleotide sequence effective to bind by sequence-specific hybridization to a template region of hTR. Preferably, the amount of the telomerase inhibitor is effective to inhibit the proliferation of cancer cells in the subject when the telomerase inhibitor is administered alone.

The two inhibitors inhibitor may be administered to the subject as a composition containing both compounds. The enhancement of treatment efficacy may be evidenced, for example, by an increased survival time of the subject, or by an inhibition of tumor growth in the subject, relative to treatment with the EGF pathway inhibitor alone.

The oligonucleotide may be 10-20 bases in length. Preferably, the oligonucleotide is 13-20 bases in length and includes the sequence identified by SEQ ID NO: 12 (5'-TAGGGTTA-GACAA-3'). An exemplary telomerase inhibitor is the compound identified as GRN163L, or an analog thereof. This compound has (i) N3'→P5' thiophosphoramidate internucleoside linkages; (ii) the sequence identified as SEQ ID NO:12; and (iii) a palmitoyl (C16) moiety linked to the 5' end of the oligonucleotide through a glycerol or aminoglycerol linker. An exemplary anti-EGF receptor antibody is the humanized anti-HER2 antibody Trastuzumab.

Also disclosed is a kit for use in carcinoma therapy, comprising (a) a dose of an EGF pathway inhibitor, such as an anti-EGF receptor antibody, effective, when administered alone, to inhibit the proliferation of carcinoma cells in the subject, and (b) a dose of an oligonucleotide telomerase inhibitor having nuclease-resistant intersubunit linkages, and an oligonucleotide sequence effective to bind by sequence-specific hybridization to a template region of hTR. In one embodiment, the telomerase inhibitor is provided in an amount effective, when administered alone, to inhibit proliferation of cancer cells in the subject.

In an exemplary embodiment, the anti-EGF receptor antibody is an anti-HER2 antibody such as trastuzumab, and the telomerase inhibitor is the compound identified as GRN163L, or an analog thereof. The latter compound has (i) N3'→P5' thiophosphoramidate internucleoside linkages in the oligonucleotide; (ii) the sequence identified as SEQ ID NO: 12; and (iii) a palmitoyl (C16) moiety linked to the 5' end of the oligonucleotide through a glycerol or aminoglycerol linker.

Also provided is a kit comprising a telomerase inhibitor and an anti-EGF receptor antibody, for use in treating a carcinoma. Such therapy preferably comprises administering the antibody to a subject, either preceding, following, or concomitantly with administration of the telomerase inhibitor. The telomerase inhibitor is preferably a nuclease-resistant oligonucleotide which binds in a sequence-specific manner to the template region of hTR.

In a related aspect, the invention provides a kit containing a dose of an oligonucleotide telomerase inhibitor having nuclease-resistant intersubunit linkages and an oligonucleotide sequence effective to bind by sequence-specific hybridization to a template region of hTR, preferably in an amount effective to inhibit proliferation of cancer cells in a subject. The kit preferably includes an insert with instructions for administration of the telomerase inhibitor. The insert may provide a user with one set of instructions for using the inhibitor in monotherapy and a separate set of instructions for using the inhibitor in combination with an EGF pathway inhibitor, such as an anti-EGF receptor antibody.

The set of instructions for the combination therapy may recommend (i) a lower dose of the telomerase inhibitor, when used in combination with the EGF pathway inhibitor, (ii) a lower dose of the EGF pathway inhibitor, when used in combination with the telomerase inhibitor, and/or (iii) a different dosing regimen for one or both inhibitors than would normally be recommended.

Also provided is the use of a telomerase inhibitor for preparation of a medicament for use in treatment of carcinoma in a subject, wherein the treatment comprises administering said telomerase inhibitor to a subject in combination with an EGF pathway inhibitor, such as an anti-EGF receptor antibody, as exemplified by anti-HER2 antibody trastuzumab. The treatment may comprise administering the antibody to the subject either preceding, following, or concomitantly with the telomerase inhibitor, which is preferably a nuclease-resistant oligonucleotide which binds in a sequence-specific manner to the template region of hTR.

In a related aspect, the invention provides the use of an EGF pathway inhibitor and a telomerase inhibitor, in the manufacture of a medicament for treating cancer in a subject. Preferred and/or exemplary inhibitors and cancer indications are as set out above.

Further disclosed is the use of a telomerase inhibitor in the manufacture of a medicament for treating breast or ovarian cancer in a subject who is being treated with an EGF pathway inhibitor, such as an anti-EGF receptor antibody, for purposes of enhancing the anti-cancer efficacy of the antibody in the subject.

These and other objects and features of the invention will become more fully apparent when the following detailed description of the invention is read in conjunction with the accompanying drawings.

DETAILED DESCRIPTION OF THE INVENTION

I. Definitions

Figure 1:
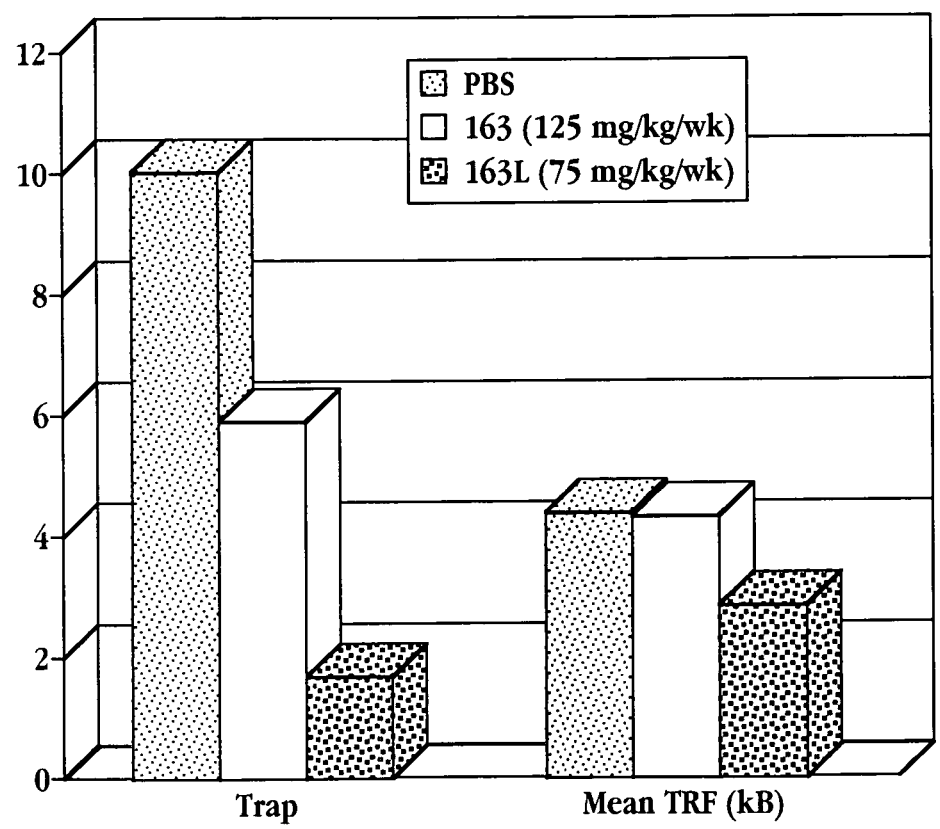
FIGS. 1 and 2 show enhancement of telomerase inhibiting activity of an NPS oligonucleotide hTR template inhibitor (GRN163) by conjugation to a lipid (to produce GRN163L), in human myeloma tumor xenografts (FIG. 1) and liver cells (FIG. 2), respectively, in mice.

The terms below have the following meanings unless indicated otherwise.

A "polynucleotide" or "oligonucleotide" refers to a ribose and/or deoxyribose nucleoside subunit polymer or oligomer having between about 2 and about 200 contiguous subunits. The nucleoside subunits can be joined by a variety of intersubunit linkages, including, but not limited to, phosphodiester, phosphotriester, methylphosphonate, P3'→N5' phosphoramidate, N3'→P5' phosphoramidate, N3'→'P5' thiophosphoramidate, and phosphorothioate linkages. The term also includes such polymers or oligomers having modifications, known to one skilled in the art, to the sugar (e.g., 2' substitutions), the base (see the definition of "nucleoside" below), and the 3' and 5' termini. In embodiments where the oligonucleotide moiety includes a plurality of intersubunit linkages, each linkage may be formed using the same chemistry, or a mixture of linkage chemistries may be used. When an oligonucleotide is represented by a sequence of letters, such as "ATGUCCTG," it will be understood that the nucleotides are in 5'→3' order from left to right. Representation of the base sequence of the oligonucleotide in this manner does not imply the use of any particular type of internucleoside subunit in the oligonucleotide.

The term "nucleoside" includes the natural nucleosides, including 2'-deoxy and 2'-hydroxyl forms, e.g., as described in Komberg and Baker, DNA Replication, 2nd Ed. (Freeman, San Francisco, 1992), and analogs. "Analogs", in reference to nucleosides, includes synthetic nucleosides having modified nucleobase moieties (see definition of "nucleobase" below) and/or modified sugar moieties, e.g., described generally by Scheit, *Nucleotide Analogs* (John Wiley, New York, 1980). Such analogs include synthetic nucleosides designed to enhance binding properties, e.g., stability, specificity, or the like, such as disclosed by Uhlmann and Peyman (*Chemical Reviews* 90:543-584, 1990). An oligonucleotide containing such nucleosides, and which typically contains synthetic nuclease-resistant internucleoside linkages, may itself be referred to as an "analog".

A "nucleobase" includes (i) native DNA and RNA nucleobases (uracil, thymine, adenine, guanine, and cytosine), (ii) modified nucleobases or nucleobase analogs (e.g., 5-methylcytosine, 5-bromouracil, or inosine) and (iii) nucleobase analogs. A nucleobase analog is a compound whose molecular structure mimics that of a typical DNA or RNA base.

An oligonucleotide having "nuclease-resistant linkages" refers to one whose backbone has subunit linkages that are substantially resistant to nuclease cleavage, in non-hybridized or hybridized form, by common extracellular and intracellular nucleases in the body; that is, the oligonucleotide shows little or no nuclease cleavage under normal nuclease conditions in the body to which the oligonucleotide is exposed. The N3'→P5' phosphoramidate (NP) or N3'→P5' thiophosphoramidate (NPS) linkages described below are nuclease resistant.

The term "lipid" is used broadly herein to encompass substances that are soluble in organic solvents, but sparingly soluble, if at all, in water. The term lipid includes, but is not limited to, hydrocarbons, oils, fats (such as fatty acids and glycerides), sterols, steroids and derivative forms of these compounds. Preferred lipids are fatty acids and their derivatives, hydrocarbons and their derivatives, and sterols, such as cholesterol.

Fatty acids usually contain even numbers of carbon atoms in a straight chain (commonly 12-24 carbons) and may be saturated or unsaturated, and can contain, or be modified to contain, a variety of substituent groups. For simplicity, the term "fatty acid" also encompasses fatty acid derivatives, such as fatty or esters.

The term "hydrocarbon" encompasses compounds that consist only of hydrogen and carbon, joined by covalent bonds. The term encompasses open chain (aliphatic) hydrocarbons, including straight chain and branched hydrocarbons, and saturated as well as mono- and poly-unsaturated hydrocarbons. The term also encompasses hydrocarbons containing one or more aromatic rings.

As used herein, the term "lipid" also includes amphipathic compounds containing both lipid and hydrophilic moieties.

An "hTR template inhibitor" is a compound that blocks the template region (the region spanning nucleotides 30-67 of SEQ ID NO: 1 herein) of the RNA component of human telomerase, thereby inhibiting the activity of the enzyme. The inhibitor is typically an oligonucleotide that is able to hybridize to this region. Preferably, the oligonucleotide includes a sequence effective to hybridize to a more specific portion of this region, having sequence 5'-CUAACCCUAAC-3' spanning nucleotides 46-56 of SEQ ID NO: 1 herein.

A "carcinoma" is a malignant tumor of epithelial-cell origin, that is, a malignant tumor that begins in the lining layer (epithelial cells) of organs. At least 80% of all cancers are carcinomas, and include breast cancer, both ductal and lobular carcinomas of the breast; ovarian cancer; basal-cell carcinoma, the most common non-melanoma skin cancer; squamous cell carcinoma, a common form of skin cancer and the most common type of lung cancer; hepatocellular carcinoma, the most common form of liver cancer; renal cell carcinoma, a malignant tumor located of the kidneys; and transitional cell carcinoma, a type of cancer that develops in the lining of the bladder, ureter, or renal pelvis. The cancer cells making up a carcinoma are referred to as "carcinoma cells."

A compound is said to "inhibit the proliferation of carcinoma cells" if the proliferation of cells in the presence of the compound is less than that observed in the absence of the compound. That is, proliferation of the cells is either slowed or halted in the presence of the compound. Inhibition of carcinoma cells may be evidenced, for example, by reduction in the number of cells or rate of expansion of cells, reduction in tumor mass or the rate of tumor growth, or increase in survival rate of a subject being treated.

An "epithelial growth factor (EGF) pathway inhibitor" is a compound that inhibits cellular growth and/or division events triggered by activation of and signaling by an EGF receptor, such as by the binding of EGF or ATP to the receptor. EGF receptors are members of the ErbB family receptors, a sub-family of four closely related receptor tyrosine kinases: EGFR (ErbB-1 or HER1), HER2/c-neu (ErbB-2 or HER2)), Her3 (ErbB-3) and Her4 (ErbB-4). EGFR (ErbB-1) receptor exists on the cell surface and is activated by binding of specific ligands, including epidermal growth factor and transforming growth factor α (TGFα). The related ErbB3 and ErbB4 receptors are activated by neuregulins (NRGs). ErbB2 (HER2) has no known direct activating ligand, and may be in an activated state constitutively.

Upon activation, EGFR undergoes a transition from an inactive monomeric form to an active homodimer—although there is some evidence that preformed inactive dimers may also exist before ligand binding. In addition to forming homodimers after ligand binding, EGFR may pair with another member of the ErbB receptor family, such as ErbB2/Her2/neu, to create an activated heterodimer. There is also evidence to suggest that clusters of activated EGFRs form, although it remains unclear whether this clustering is important for activation itself or occurs subsequent to activation of individual dimers.

"Administration of a telomerase inhibitor to a subject is effective to "enhance the anti-cancer treatment efficacy of an EGF pathway inhibitor," such as an anti-EGF receptor antibody, if the subject shows a reduced rate of tumor growth and/or an enhanced survival rate with combined therapy over therapy with the EGF pathway inhibitor alone.

An anti-EGF receptor antibody is an antibody that binds specifically to an EGF receptor, i.e., EGFR (ErbB-1 or HER1), HER2/c-neu (ErbB-2 or HER2)), Her3 (ErbB-3) or Her4 (ErbB-4), to block signaling of the receptor related to cell growth and division. The antibody may encompass an immunoglobulin molecule comprised of four polypeptide chains, two heavy (H) chains and two light (L) chains interconnected by disulfide bonds, and various fragments and variants thereof. For example, the antibody may lack the Fc fragment of naturally formed antibodies, and may include (i) an Fab fragment, which is a monovalent fragment consisting of the $V_L$, $V_H$, $C_L$ and $C_H1$ domains; (ii) a F(ab')$_2$ fragment, a bivalent fragment comprising two Fab fragments linked by a disulfide bridge at the hinge region; (iii) an Fd fragment consisting of the $V_H$ and $C_H1$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR). In particular, although the two domains of the Fv fragment, $V_L$ and $V_H$, are coded for by separate genes, they can be joined by recombinant methods, by a synthetic linker that enables them to be made as a single protein chain in which the $V_L$ and $V_H$ regions pair to form monovalent molecules known as single chain variable fragment or scFv antibodies; see e.g., Bird et al. (1988) Science 242:423-426; and Huston et al. (1988) Proc. Natl. Acad. Sci. USA 85:5879-5883), and the term; antibody lacking an Fc fragment also encompasses antibodies having this scFv format.

The term human or humanized antibodies refers to an antibody having one or more amino acid residues introduced into it from a source which is non-human. These non-human amino acid residues are referred to herein as "import" residues, which are typically taken from an "import" antibody domain, particularly a variable domain. An import residue, sequence, or antibody has a desired affinity and/or specificity, or other desirable antibody biological activity as discussed herein. In general, the humanized antibody will comprise substantially all of at least one, and typically two, variable domains (Fab, Fab', F(ab').sub.2, Fabc, Fv) in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. Ordinarily, the antibody will contain both the light chain as well as at least the variable domain of a heavy chain. The antibody also may include the CH1, hinge, CH2, CH3, and CH4 regions of the heavy chain. humanized or human monoclonal antibodies refers to monoclonal antibodies.

II. Treatment of Cancer with EGF Pathway Inhibitors

This section considers the treatment of carcinomas by administration of an EGF pathway inhibitor alone, where the inhibitor may be either an anti-EGF receptor antibody or a small molecule inhibitor of the receptor tyrosine kinase activity.

A. Anti-EGF Receptor Antibody.

Several anti-cancer therapies are based on the binding of an anti-EGF receptor by an anti-EGF receptor antibody. The anti-HER2 antibody trastuzumab (Herceptin®) and the anti-EGFR antibody cetuximab (Erbitux®) have demonstrated that inhibition of EGF signaling is an effective mechanism for treating certain solid tumors.

Trastuzumab is a murine monoclonal antibody known as muMAb4D5 (Fendly, B. M. et al., Cancer Res. 50:1550-1558 (1990)), directed against the extracellular domain (ECD) of p185.sup.HER2, specifically inhibits the growth of tumor cell lines overexpressing p185.sup.HER2 in monolayer culture or in soft agar (Hudziak, R. M. et al., Molec. Cell. Biol. 9:1165-1172 (1989); Lupu, R. et al., Science 249:1552-1555 (1990)). MuMAb4D5 also has the potential of enhancing tumor cell sensitivity to tumor necrosis factor, an important effector molecule in macrophage-mediated tumor cell cytotoxicity (Hudziak, supra, 1989; Shepard, H. M. and Lewis, G. D. J. Clinical Immunology 8:333-395 (1988)). Thus muMAb4D5 has potential for clinical intervention in and imaging of carcinomas in which p185.sup.HER2 is overexpressed. The muMAb4D5 and its uses are described in PCT application WO 89/06692 published Jul. 27, 1989.

Human or humanized anti-HER2 antibodies can be obtained by using human hybridomas (Cole et al., Monoclonal Antibodies and Cancer Therapy, Alan R. Liss, p. 77 (1985)). Techniques developed for the production of "chimeric antibodies" (Morrison et al., Proc. Natl. Acad. Sci. 81, 6851 (1984); Neuberger et al., Nature 312, 604 (1984); Takeda et al., Nature 314, 452 (1985)) by splicing the genes from a mouse antibody molecule of appropriate antigen specificity together with genes from a human antibody molecule of appropriate biological activity (such as ability to activate human complement and mediate ADCC) can be used; such antibodies are within the scope of this invention.

As noted, an anti-HER2 antibody, such as trastuzumab, is indicated particularly for breast cancer characterized by elevated HER2 levels on the surface of the carcinoma cells, and for ovarian cancers with elevated levels of surface HER2 receptor. Detectable concentrations of the circulating extracellular domain of the HER2 receptor (shed antigen) are found in the serum of some patients with HER2 overexpressing tumors. Clinical studies in baseline serum samples revealed that 64% (286/447) of patients had detectable shed antigen, which ranged as high as 1880 ng/mL (median=11 ng/mL). The Clinical Trial Assay (CTA) may be used for immunohistochemical detection of HER2 protein overexpression. Alternatively, the DAKO HercepTest™ provides another immunohistochemical test for HER2 protein overexpression, and shows strong correlation with the CTA test. However, the antibody may be used in treating a variety of other carcinomas, which generally have surface-bound HER2 receptor.

Trastuzumab is given every week, every two weeks, or every three weeks by a needle placed into a vein (intravenously). In clinical studies, short duration intravenous infusions of 10 to 500 mg once weekly demonstrated dose-dependent pharmacokinetics. Mean half-life increased and clearance decreases with increasing dose level. The half-life averaged 1.7 and 12 days at the 10 and 500 mg dose levels, respectively. Trastuzumab's volume of distribution was approximately that of serum volume (44 mL/kg). At the highest weekly dose studied (500 mg), mean peak serum concentrations were 377 microgram/mL. In studies using a loading dose of 4 mg/kg followed by a weekly maintenance dose of 2 mg/kg, a mean half-life of 5.8 days (range=1 to 32 days) was observed. Between weeks 16 and 32, trastuzumab serum concentrations reached a steady-state with a mean trough and peak concentrations of approximately 79 microgram/mL and 123 microgram/mL, respectively.

Data suggest that the disposition of trastuzumab is not altered based on age or serum creatinine (up to 2.0 mg/dL). Patients with higher baseline shed antigen levels were more likely to have lower serum trough concentrations. However, with weekly dosing, most patients with elevated shed antigen levels achieved target serum concentrations of Trastuzumab by week 6.

Cetuximab (Erbitux), a chimeric anti-EGF receptor antibody specific for EGFR, may be indicated, for example, for the treatment of metastatic colorectal cancer and head and neck cancer, or for the treatment of EGFR-expressing, metastatic colorectal carcinoma in patients who are refractory to irinotecan-based chemotherapy.

Pretreatment with an $H_1$ antagonist (eg, 50 mg of diphenhydramine IV) may be recommended in cetuximab therapy.

The recommended dose of cetuximab, in combination with radiation therapy, is 400 mg/m² as an initial loading dose (first infusion) administered as a 120-minute IV infusion (maximum infusion rate 5 mL/min) one week prior to initiation of a course of radiation therapy. The recommended weekly maintenance dose (all other infusions) is 250 mg/m² infused over 60 minutes (maximum infusion rate 5 mL/min) weekly for the duration of radiation therapy (6-7 weeks). In clinical studies, cetuximab was administered 1 hour prior to radiation therapy.

The recommended dosing regimen for single-agent cetuximab in the treatment of recurrent or metastatic squamous cell carcinoma of the head and neck is a 400-mg/m² initial dose, (first infusion) administered as a 120-minute IV infusion (maximum infusion rate 5 mL/min). The recommended weekly maintenance dose (all other infusions) is 250 mg/m² infused over 60 minutes (maximum infusion rate 5 mL/min).

B. Small Molecules Inhibitors of the EGF Pathway.

A number of small molecule anti-cancer agents that target the EGF pathway have also been proposed in anti-cancer treatment. Erlotinib (Tarceva®) and gefitinib (Iressa®) specifically target the tyrosine kinase activity of EGFR, which may be highly expressed and occasionally mutated in various forms of cancer. The drug molecules bind in a reversible fashion to the adenosine triphosphate (ATP) binding site of the receptor, effectively blocking autophosphorylation of EGFR homodimers, and thus blocking the signal cascade to the nucleus. Both compounds have shown a survival benefit in the treatment of lung cancer in phase III trials, and have been approved for the treatment of locally advanced or metastatic non small cell lung cancer.

Erlotinib is a quinazolinamine with the chemical name N-(3-ethynylphenyl)-6,7-bis(2-methoxyethoxy)-4-quinazolinamine and is provided (Tarceva®) as the hydrochloride salt which has the following structural formula:

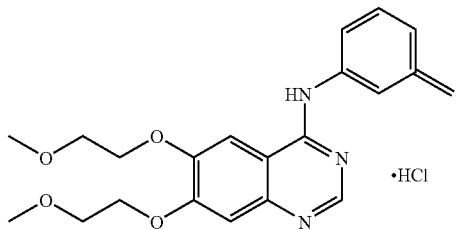

Aqueous solubility of erlotinib hydrochloride is dependent on pH with increased solubility at a pH of less than 5 due to protonation of the secondary amine. Over the pH range of 1.4 to 9.6, maximal solubility of approximately 0.4 mg/mL occurs at a pH of approximately 2. Tarceva® tablets are available in three dosage strengths containing erlotinib hydrochloride (27.3 mg, 109.3 mg and 164 mg) equivalent to 25 mg, 100 mg and 150 mg erlotinib. Erlotinib is about 60% absorbed after oral administration and its bioavailability is substantially increased by food to almost 100%. Its half-life is about 36 hours and it is cleared predominantly by CYP3A4 metabolism. Peak plasma levels occur 4 hrs after dosing. Food increases bioavailability substantially, to almost 100%.

The drug is indicated for small non-small-cell lung cancer, advanced pancreatic cancer, and a variety of other carcinomas, particularly those characterized by overexpression of EGFR, such as colorectal cancer and carcinomas of the head and neck.

Gefitinib (Iressa®) is another in the class of small molecule drugs that inhibit the tyrosine kinase activity of the epidermal growth factor receptor. Like erlotinib, the drug competes with the binding of ATP to the intracellular tyrosine kinase domain of EGFR, thereby inhibiting receptor autophosphorylation and blocking downstream signal transduction.

Gefitinib is typically administered at a dose of 250 or 500 mg orally once daily. The drug is indicated as a monotherapy for the treatment of patients with locally advanced or metastatic NSCLC after failure of both platinum-based and docetaxel chemotherapies[8].

III. Treatment of Cancer with a Telomerase Inhibitor

Telomerase is a ribonucleoprotein that catalyzes the addition of telomeric repeat sequences (having the sequence 5'-TTAGGG-3' in humans) to chromosome ends. See e.g. Blackburn, 1992, *Ann. Rev. Biochem.* 61:113-129. The enzyme is expressed in most cancer cells but not in mature somatic cells. Loss of telomeric DNA may play a role in triggering cellular senescence; see Harley, 1991, *Mutation Research* 256:271-282. A variety of cancer cells have been shown to be telomerase-positive, including cells from cancer of the skin, connective tissue, adipose, breast, lung, stomach, pancreas, ovary, cervix, uterus, kidney, bladder, colon, prostate, central nervous system (CNS), retina and hematologic tumors (such as myeloma, leukemia and lymphoma). Targeting of telomerase can be effective in providing treatments that discriminate between malignant and normal cells to a high degree, avoiding many of the deleterious side effects that can accompany chemotherapeutic regimens which target dividing cells indiscriminately.

Inhibitors of telomerase identified to date include oligonucleotides, preferably oligonucleotides having nuclease resistant linkages, as well as small molecule compounds.

A. Small Molecule Compounds

Small molecule inhibitors of telomerase include, for example, BRACO19 ((9-(4-(N,N-dimethylamino)phenylamino)-3,6-bis(3-pyrrolodino propionamido)acridine (see *Mol. Pharmacol.* 61(5):1154-62, 2002); DODC (diethyloxadicarbocyanine), and telomestatin. These compounds may act as G-quad stabilizers, which promote the formation of an inactive G-quad configuration in the RNA component of telomerase. Other small molecule inhibitors of telomerase include BIBR1532 (2-[(E)-3-naphthen-2-yl but-2-enoylamino]benzoic acid) (see Ward & Autexier, *Mol. Pharmacol.* 68:779-786, 2005; also *J. Biol. Chem.* 277(18):15566-72, 2002); AZT and other nucleoside analogs, such as ddG and ara-G (see, for example, U.S. Pat. Nos. 5,695,932 and 6,368,789), and certain thiopyridine, benzo[b]thiophene, and pyrido[b]thiophene derivatives, described by Gaeta et al. in U.S. Pat. Nos. 5,767,278, 5,770,613, 5,863,936, 5,656,638 and 5,760,062. One example is 3-chlorobenzo[b]thiophene-2-carboxy-2'-[(2,5-dichlorophenyl amino)thia]hydrazine, described in U.S. Pat. No. 5,760,062.

B. Oligonucleotide-Based Telomerase Inhibitors: Sequence and Composition

The genes encoding both the protein and RNA components of human telomerase have been cloned and sequenced (see U.S. Pat. Nos. 6,261,836 and 5,583,016, respectively, both of which are incorporated herein by reference). Oligonucleotides can be targeted against the mRNA encoding the telomerase protein component (the human form of which is known as human telomerase reverse transcriptase, or hTERT) or the RNA component of the telomerase holoenzyme (the human form of which is known as human telomerase RNA, or hTR).

The nucleotide sequence of the RNA component of human telomerase (hTR) is shown in the Sequence Listing below (SEQ ID NO: 1), in the 5'→3' direction. The sequence is shown using the standard abbreviations for ribonucleotides; those of skill in the art will recognize that the sequence also represents the sequence of the cDNA, in which the ribonucleotides are replaced by deoxyribonucleotides, with uridine (U) being replaced by thymidine (T). The template sequence of the RNA component is located within the region defined by nucleotides 46-56 of SEQ ID NO: 1 (5'-CUAACCCUAAC-3'), which is complementary to a telomeric sequence composed of about one-and-two-thirds telomeric repeat units. The template region functions to specify the sequence of the telomeric repeats that telomerase adds to the chromosome ends and is essential to the activity of the telomerase enzyme (see e.g. Chen et al., *Cell* 100: 503-514, 2000; Kim et al., *Proc. Natl. Acad. Sci. USA* 98 (14):7982-7987, 2001). The design of antisense, ribozyme or small interfering RNA (siRNA) agents to inhibit or cause the destruction of mRNAs is well known (see, for example, Lebedeva, I, et al. Annual Review of Pharmacology and Toxicology, Vol. 41: 403-419, April 2001; Macejak, D, et al., Journal of Virology, Vol. 73 (9): 7745-7751, September 1999, and Zeng, Y. et al., PNAS Vol. 100 (17) p. 9779-9784, Aug. 19, 2003) and such agents may be designed to target the hTERT mRNA and thereby inhibit production of hTERT protein in a target cell, such as a cancer cell (see, for example, U.S. Pat. Nos. 6,444,650 and 6,331,399).

Oligonucleotides targeting hTR (that is, the RNA component of the enzyme) act as inhibitors of telomerase enzyme activity by blocking or otherwise interfering with the interaction of hTR with the hTERT protein, which interaction is necessary for telomerase function. See, for example, Villeponteau et al., U.S. Pat. No. 6,548,298.

A preferred target region of hTR is the template region, spanning nucleotides 30-67 of SEQ ID NO:1. Oligonucleotides targeting this region are referred to herein as "hTR template inhibitors" (see e.g. Herbert et al., *Oncogene* 21(4): 638-42 (2002).) Preferably, such an oligonucleotide includes a sequence which is complementary or near-complementary to some portion of the 11-nucleotide region having sequence 5'-CUAACCCUAAC-3', spanning nucleotides 46-56 of SEQ ID NO: 1.

Another preferred target region is the region spanning nucleotides 137-179 of hTR (see Pruzan et al., *Nucl. Acids Research*, 30:559-568, 2002). Within this region, the sequence spanning 141-153 is a preferred target. PCT publication WO 98/28442 describes the use of oligonucleotides of at least 7 nucleotides in length to inhibit telomerase, where the oligonucleotides are designed to be complementary to accessible portions of the hTR sequence outside of the template region, including nucleotides 137-196, 290-319, and 350-380 of hTR. Preferred hTR targeting sequence are given below, and identified by SEQ ID NOS: 2-22.

The region of the therapeutic oligonucleotide that is targeted to the hTR sequence is preferably exactly complementary to the corresponding hTR sequence. While mismatches may be tolerated in certain instances, they are expected to decrease the specificity and activity of the resultant oligonucleotide conjugate. In particular embodiments, the base sequence of the oligonucleotide is thus selected to include a sequence of at least 5 nucleotides exactly complementary to the hTR target, and enhanced telomerase inhibition may be obtained if increasing lengths of complementary sequence are employed, such as at least 8, at least 10, at least 12, at least 13 or at least 15 nucleotides exactly complementary to the hTR target. In other embodiments, the sequence of the oligonucleotide includes a sequence of from at least 5 to 20, from at least 8 to 20, from at least 10 to 20 or from at least 10 to 15 nucleotides exactly complementary to the hTR target sequence.

Optimal telomerase inhibitory activity may be obtained when the full length of the oligonucleotide is selected to be complementary to the hTR target sequence. However, it is not necessary that the full length of the oligonucleotide is exactly complementary to the target sequence, and the oligonucleotide sequence may include regions that are not complementary to the target sequence. Such regions may be added, for example, to confer other properties on the compound, such as sequences that facilitate purification. Alternatively, an oligonucleotide may include multiple repeats of a sequence complementary to an hTR target sequence.

If the oligonucleotide is to include regions that are not complementary to the target sequence, such regions are typically positioned at one or both of the 5' or 3' termini. Exemplary sequences targeting human telomerase RNA (hTR) include the following:

| hTR Targeting Sequence | Region of SEQ ID NO: 1 | SEQ ID NO: |
|---|---|---|
| ACATTTTTGTTTGCTCTAG | 160-179 | 2 |
| GCTCTAGAATGAACGGT GGAAGGCGGCAGG | 137-166 | 3 |
| GTGGAGGCGGCAGG | 137-151 | 4 |
| GGAAGGCGGCAGG | 137-149 | 5 |
| GTGGAAGGCGGCA | 139-151 | 6 |
| GTGGAAGGCGG | 141-151 | 7 |
| CGGTGGAAGGCGG | 141-153 | 8 |
| ACGGTGGAAGGCG | 142-154 | 9 |
| AACGGTGGAAGGCGGC | 143-155 | 10 |
| ATGAACGGTGGAAGGCGG | 144-158 | 11 |
| TAGGGTTAGACAA | 42-54 | 12 |
| CAGTTAGGGTTAG | 46-58 | 13 |
| TAGGGTTAGACA | 42-53 | 14 |
| TAGGGTTAGAC | 42-52 | 15 |
| GTTAGGGTTAG | 46-56 | 16 |
| GTTAGGGTTAGAC | 44-56 | 17 |
| GTTAGGGTTAGACAA | 42-56 | 18 |
| GGGTTAGAC | 44-52 | 19 |
| CAGTTAGGG | 50-58 | 20 |
| CCCTTCTCAGTT | 54-65 | 21 |
| CGCCCTTCTCAG | 56-67 | 22 |

The internucleoside linkages in the oligonucleotide may include any of the available oligonucleotide chemistries, e.g. phosphodiester, phosphotriester, methylphosphonate, P3'→N5' phosphoramidate, N3'→P5' phosphoramidate, N3'→P5' thiophosphoramidate, and phosphorothioate. Typically, but not necessarily, all of the internucleoside linkages within the oligonucleotide will be of the same type, although the oligonucleotide component may be synthesized using a mixture of different linkages.

In preferred embodiments, the oligonucleotide has at least one N3'→P5' phosphoramidate (NP) or N3'→P5' thiophosphoramidate (NPS) linkage, which linkage may be represented by the structure: 3'-(—NH—P(=O)(—XR)—O—)-5', wherein X is O or S and R is selected from the group consisting of hydrogen, alkyl, and aryl; and pharmaceutically acceptable salts thereof, when XR is OH or SH. More preferably, the oligonucleotide includes all NP or, most preferably, all NPS linkages.

A particularly preferred sequence for an hTR template inhibitor oligonucleotide is the sequence complementary to nucleotides 42-54 of SEQ ID NO: 12 above. The oligonucleotide having this sequence (TAGGGTTAGACA) and N3'→P5' thiophosphoramidate (NPS) linkages is designated showed moderate activity. The effect is clearly sequence-specific, as shown by the mismatch and non-targeting sequences in the table.

The oligonucleotide GRN163 administered alone has shown inhibitory activity in vitro in cell culture, including epidermoid carcinoma, breast epithelium, renal carcinoma, renal adenocarcinoma, pancreatic, brain, colon, prostate, leukemia, lymphoma, myeloma, epidermal, cervical, ovarian and liver cancer cells.

The oligonucleotide GRN163 has also been tested and shown to be therapeutically effective in a variety of animal tumor models, including ovarian and lung, both small cell and non-small cell.

TABLE 1

Inhibition of Telomerase by NPS Oligonucleotides: Biochemical (FlashPlate) Assay

| Sequence, 5' to 3' | Description | IC$_{50}$, nM |
|---|---|---|
| TAGGGTTAGACAA SEQ ID NO: 12 | 13-mer (GRN163) | 0.045 ± 0.007 |
| TAGGTGTAAGCAA (SEQ ID NO: 23) | Mismatch of GRN163 sequence | 80 ± 31 |
| TTGTCTAACCCTA (SEQ ID NO: 24) | Complement of GRN163 sequence | 1000 ± 46 |
| TAGGGTTAGACAA ATCCCAATCTGTT | Duplex of GRN163 sequence | 8.9 ± 3.0 |
| CAGTTAGGGTTAG (SEQ ID NO: 13) | Alternative targeting 13-mer | 0.049 ± 0.007 |
| TAGGGTTAGACA (SEQ ID NO: 14) | 12-mer; truncation of GRN163 sequence | 0.36 ± 0.2 |
| TAGGGTTAGAC (SEQ ID NO: 15) | 11-mer; truncation of GRN163 sequence | 0.85 ± 0.35 |
| GTTAGGGTTAG (SEQ ID NO: 16) | Alternative targeting 11-mer | 0.51 ± 0.13 |
| GTTGAGTGTAG (SEQ ID NO: 25) | Mismatch of alternative targeting 11-mer | 177 ± 93 |
| TAGGGTTAGACAA (SEQ ID NO: 12) | 13-mer (GRN163 sequence) with NP backbone | 0.7 ± 0.1 |
| TAGGTGTAAGCAA (SEQ ID NO: 23) | Mismatch of GRN163 sequence with NP backbone | >1000 |
| TTAGGG (SEQ ID NO: 26) | Telomere repeat unit | >1000 |
| TTTTTTTTTT (SEQ ID NO: 27) | Oligo-T 10-mer | >1000 | herein as GRN163. See, for example, Asai et al., *Cancer Research* 63:3931-3939 (2003); Gryaznov et al., *Nucleosides Nucleotides Nucleic Acids* 22 (5-8):577-81 (2003).

As shown in Table 1 below, this oligonucleotide (first row of table) inhibits telomerase at low concentrations in a biochemical assay (FlashPlate™; see Experimental Section). An alternative 13-mer, having the sequence CAGTTAGGGTTAG SEQ ID NO: 13, complementary to nucleotides 46-58 of SEQ ID NO: 1 (fifth row of table), showed near-equivalent activity in the FlashPlate™ assay. The corresponding NP-linked oligonucleotide, and shorter (11- and 12-mer) oligonucleotides targeting the same region (complementary to nucleotides 42-53 and 42-42, respectively, of SEQ ID NO: 1), C. Lipid-Oligonucleotide Conjugates Preferably, the oligonucleotide-based enzyme inhibitor includes at least one covalently linked lipid group (see US Pubn. No. 2005/0113325, which is incorporated herein by reference). This modification provides superior cellular uptake properties, such that an equivalent biological effect may be obtained using smaller amounts of the conjugated oligonucleotide compared to the unmodified form. When applied to the human therapeutic setting, this may translate to reduced toxicity risks, and cost savings.

The lipid group L is typically an aliphatic hydrocarbon or fatty acid, including derivatives of hydrocarbons and fatty acids, with examples being saturated straight chain compounds having 14-20 carbons, such as myristic (tetradecanoic) acid, palmitic (hexadecanoic) acid, and stearic (octadecanoic) acid, and their corresponding aliphatic hydrocarbon forms, tetradecane, hexadecane and octadecane. Examples of other suitable lipid groups that may be employed are sterols, such as cholesterol, and substituted fatty acids and hydrocarbons, particularly polyfluorinated forms of these groups. The scope of the lipid group L includes derivatives such as amine, amide, ester and carbamate derivatives. The type of derivative is often determined by the mode of linkage to the oligonucleotide, as exemplified below.

In one exemplary structure, the lipid moiety is palmitoyl amide (derived from palmitic acid), conjugated through an aminoglycerol linker to the 5' thiophosphate group of an NPS-linked oligonucleotide. The NPS oligonucleotide having the sequence shown for GRN163 and conjugated in this manner (as shown below) is designated GRN163L herein. In a second exemplary structure, the lipid, as a palmitoyl amide, is conjugated through the terminal 3' amino group of an NPS oligonucleotide.

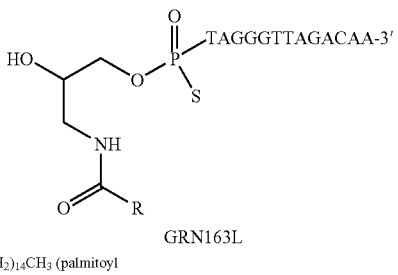

GRN163L

R = ——(CH$_2$)$_{14}$CH$_3$ (palmitoyl)

As shown in Table 2, conjugation of a single fatty acid-type lipid significantly increased telomerase inhibitory activity in cell systems relative to the unconjugated oligonucleotide.

TABLE 2

Inhibition of Telomerase by Lipid-Conjugated NPS Oligonucleotides (based on GRN163)

| Lipid Substitution | Tm (° C.) of duplex with RNA | IC$_{50}$ in vitro, HT-3 cells, nM |
|---|---|---|
| none (GRN163) | 70.0 | 1600 |
| 3'-palmitic (GRN163L) | 66.5 | 160 |
| 3'-stearic | 67.1 | 140 |
| 3'-(bis)stearic | ~40 | 1960 |
| 3'-oleic | 66.8 | 930 |
| NH—C$_{16}$ (palmitoyl) on 3$^{rd}$ 5' residue (G) | 62.6 | 500 |
| 5'-palmitic | 65.5 | 112 |
| 3'-palmitic-5'-palmitic | 61.3 | ~10000 |
| 3'-trityl | 66.1 | 3000 |

The effect of lipid conjugation on pharmacokinetics is illustrated by the data shown in Table 3, below, for a 4 mg/kg dose administered in rats. Target organ concentrations 6 hours after administration were also more favorable for GRN163L, with approx. 4-5 μM found in liver, kidney, and fat tissue, 2-3 μM in bone marrow and spleen, and about 0.5 μM in lymph node. Distribution of the unlipidated oligonucleotide, GRN163, was primarily to the kidney (about 18 μM), with only 1 μM or less in the remaining organ tissues noted above.

Table 4 presents further data directed to telomerase inhibition in vitro by GRN163 (unconjugated) and GRN163L (lipidated) in various cancer cell lines.

TABLE 3

Comparative Pharmacokinetics of Lipidated (GRN163L) and Unlipidated (GRN163) NPS Oligonucleotide (Rat, 4 mg/kg dose)

| | GRN163 | GRN163L |
|---|---|---|
| T$_{1/2}$α, min | 17 | 20 |
| T$_{1/2}$β, hrs | 65-86 | 68-72 |
| AUC$_{0-\infty}$, μg-hr/g | 27 | 120 |
| C$_{MAX}$, μg/ml | 16 | 58 |
| % excreted in 24 h | 45 | 13 |

TABLE 4

Comparative Telomerase Inhibitory Activity of Lipidated (GRN163L) and Unlipidated (GRN163) NPS Oligonucleotide in vitro

| Cell Line | GRN163 IC$_{50}$ (μM) | GRN163L IC$_{50}$ (μM) |
|---|---|---|
| HT-3 (Cervical) | 1.62 | 0.3 |
| U251 (Glioblastoma) | 1.75 | 0.17 |
| U87 (Glioblastoma) | 0.75 | 0.11 |
| Hep3B (Hepatoma) | 6.5 | 0.36 |
| HepG2 (Hepatoma) | 2.72 | 0.48 |
| NCI-H522 (Lung) | 2.59 | 0.23 |
| RPMI 8226 (Myeloma) | 2.67 | 0.38 |
| Ovcar5 (Ovarian) | 3.74 | 0.92 |
| DU 145 (Prostate) | 1.4 | 0.15 |

Figure 2:
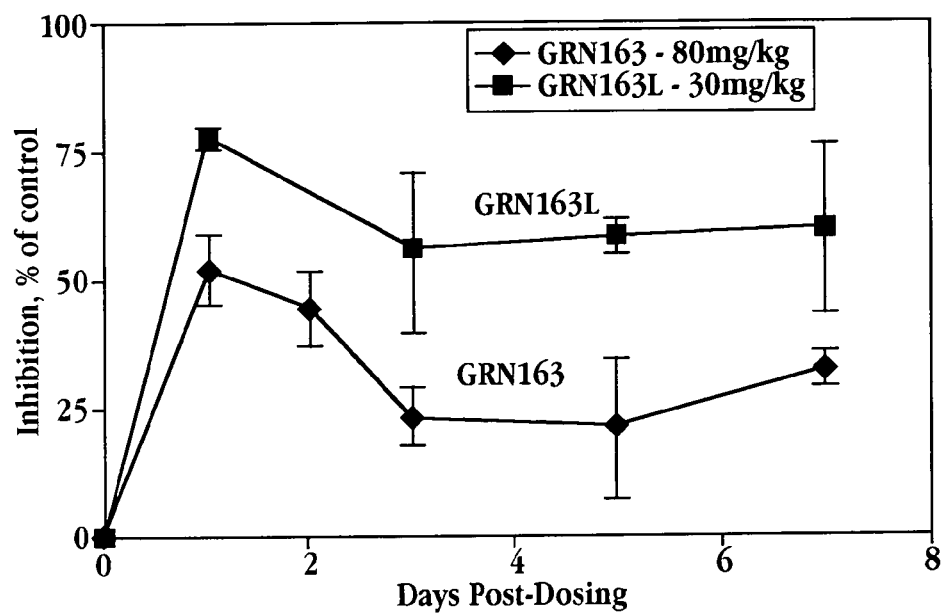

The conjugated oligonucleotide GRN163L had significantly greater telomerase inhibiting activity in vivo than the unconjugated GRN163, as demonstrated in hepatoma cell xenografts (FIG. 1) and flank CAG myeloma tumor xenografts (FIG. 2) following i.v. administration.

Administration of GRN163L inhibited tumor growth in mice (A549-luc IV lung metastases model) for at least 4 weeks after i.v. injection of cancer cells. The dosage was 1 μM biweekly for 5 weeks prior to injection of cancer cells, followed by 5 mg/kg twice weekly after injection. Controls showed substantial tumor growth, but none was apparent in the GRN163L-treated mouse.

IV. Combination Therapy with EGF Pathway and Telomerase Inhibitors

In accordance with the present invention, it has been discovered that combined exposure of cancer cells to both an EGF pathway inhibitor and a telomerase inhibitor enhances the extent to which carcinoma cell proliferation is inhibited relative to the EGF pathway inhibitor alone or the telomerase inhibitor alone. The effect is seen both for inhibition of carcinoma cell growth in vitro, where the inhibition is evidenced by a reduced rate of cell proliferation, and for in vivo treatment of cancer in a mammalian subject, where the inhibition is evidenced by a reduced rate of tumor growth and/or increased survival time of the subject being treated.

A. Combined Therapy In Vivo

In practicing the method of the invention for in vivo treatment, the subject is to be treated for a carcinoma, such as breast cancer, including either ductal and lobular carcinomas of the breast; ovarian cancer; basal-cell carcinoma, squamous cell carcinoma, non-small cell lung cancer, hepatocellular carcinoma, renal cell carcinoma, or transitional cell carcinoma, a type of cancer that develops in the lining of the bladder, ureter, or renal pelvis.

In selecting the EGF pathway inhibitor for the treatment, the subject carcinoma cells or serum may be assayed for expression or overexpression of an EGF receptor, such as EGFR or HER2, according to known methods, and as referenced above. The anti-HER2 antibody trastuzumab may be indicated, for example, in a patient having breast or ovarian cancer and elevated levels of HER2 associated with the carcinoma cells. Similarly, the anti-EGFR antibody may be indicated for non-small cell lung cancer or carcinomas of the head and where EGFR overexpression is detected. More generally, the carcinoma should be one characterized by expression, and in some cases, overexpression of an EGF receptor.

The carcinoma should also be one that is responsive to cancer-cell inhibition by telomerase inhibition. As noted above, oligonucleotide telomerase inhibitors, as exemplified by GRN163 and GRN163L, have shown inhibitory activity in vitro against human kidney, lung, pancreatic, brain, colon, prostate, breast, leukemia, lymphoma, myeloma, epidermal, cervical, ovarian and liver cancer cells, and in vivo, via local and systemic delivery, against human brain, prostate, lymphoma, myeloma, cervical, lung, and liver cancer cells. Other preferred targets include small cell lung, esophageal, head and neck, and stomach cancers.

In an exemplary treatment method, the subject is administered the EGF pathway inhibitor, e.g., anti-EGF receptor antibody, in an amount that is effective at inhibiting proliferation of carcinoma cells in the subject. The dose administered and the dosing schedule will follow, for example, known or recommended doses for the inhibitor employed, as indicated, for example, in the drug product insert or published clinical or animal-model data. One advantage of the present invention is that lower-than-normal doses of the EGF pathway inhibitor may be administered, if necessary, due to the compensating enhancement effect of the telomerase inhibitor. Such a protocol allows for a reduced dosage of the EGF pathway inhibitor, which can have significant toxic effects at higher dosages.

Thus, a kit containing a dose of the telomerase inhibitor could contain a product insert having one set of directions for using the inhibitor in monotherapy, and another set of directions for using the inhibitor in a combination therapy with an EGF pathway inhibitor, such as trastuzumab, cetuximab, erlotinib or gefitinib. The set of instructions for the combination therapy could recommend (i) a lower dose of the telomerase inhibitor, when used in combination with the EGF pathway inhibitor, (ii) a lower dose of the EGF pathway inhibitor, when used in combination with the telomerase inhibitor and/or (iii) a different dosing regimen for one of both inhibitors than would normally be recommended.

The telomerase inhibitor may be administered, before, during, or after administration of the EGF pathway inhibitor. Typically, the two inhibitors are administered in a common dosing regimen, as described below, and the two inhibitors themselves may be administered in a combined-drug composition, or separately, for example, by enteral administration of the EGF pathway inhibitor and parenteral administration of the telomerase inhibitor. However, a dosing regimen in which the telomerase inhibitor is administered before or after administering the EGF pathway inhibitor is also contemplated. For example, a person under treatment with an EGF pathway proteasome inhibitor may be subsequently placed on a combined therapy that includes telomerase inhibitor.

Alternatively, the patient may be initially administered the EGF pathway inhibitor, followed one-to-several days later with the telomerase treatment. In this regimen, the EGF pathway inhibitor may function, in part, to sensitize the cancer cells to inhibition by a telomerase inhibition, e.g., by synchronizing the cell-division cycle and/or promoting apoptosis in the cells. Preferred dose levels and dosing schedules are considered further below.

Figure 3:
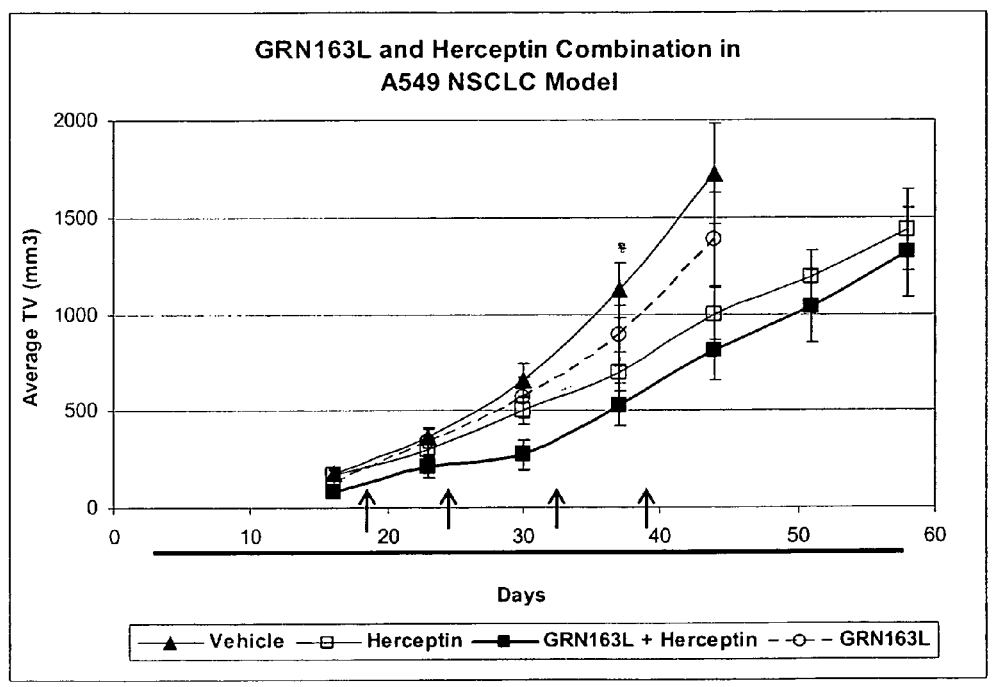
FIG. 3 illustrates the additive effect on inhibition of tumor volume (TV) achieved by co-administration of the anti-HER2 antibody trastuzumab and the telomerase inhibitor GRN163L, in an A549 non-small cell lung carcinoma model (see Section IV.A and Experimental Section D below).

In one exemplary method, the EGF pathway inhibitor is the anti-HER2 antibody trastuzumab, which is administered in combination with a telomerase-inhibitor oligonucleotide targeted against hTR. FIG. 3, for example, shows the results of the treatment method in which trastuzumab is administered in combination with the telomerase inhibitor GRN163L, for the treatment of non-small-cell lung carcinoma in a mouse xenograft model involving A549 non-small-cell lung carcinoma cells. Details of this study are given in Experimental Section D below. As seen from FIG. 3, treatment with the two inhibitors, over a 21-day treatment period (GRN163 was administered 3 times per week over the treatment period, and trastuzumab, at the times indicated by the arrows) limited tumor growth to an extent greater than either inhibitor alone. For example, at day 21 of treatment, trastuzumab alone resulted in a 38% tumor reduction, and GRN163L, in a 21% tumor reduction, while combined therapy gave a 53% reduction in tumor growth.

B. Administration

The therapeutic protocol for administering the two inhibitors in the combination therapy will depend on various factors including, but not limited to, the type of cancer, the age and general health of the patient, the aggressiveness of disease progression, the TRF length (terminal restriction fragment length; see Section V below) and telomerase activity of the diseased cells to be treated, and the ability of the patient to tolerate the agents that comprise the combination.

In general, treatment of all carcinoma and hematological malignancy types is contemplated. In selected embodiments, the target disease comprises a solid tumor; in other embodiments, the target disease comprises a hematological malignancy. An exemplary course of treatment involves multiple doses. Sequence of combination treatments will be determined by clinical compliance criteria and/or preclinical or clinical data supporting dose optimization strategies to augment efficacy or reduce toxicity of the combination treatment. In general, various combinations of the telomerase inhibitor and EGF pathway inhibitor may be employed, used either sequentially or simultaneously. For multiple dosages, the two agents may directly alternate, or two or more doses of one agent may be alternated with a single dose of the other agent, for example. Simultaneous administration of both agents may also be alternated or otherwise interspersed with dosages of the individual agents. The time between dosages may be for a period from about 1-6 hours, to about 6-12 hours, to about 12-24 hours, to about 1-2 days, to about 1-2 wk or longer following the initiation of treatment. During a course of treatment, the need to complete the planned dosings may be re-evaluated.

The compounds may be administered by direct injection of a tumor or its vasculature. Alternatively, the tumor may be infused or perfused with the therapeutic compounds using any suitable delivery vehicle. The compounds may be administered locally to an affected organ. Systemic administration may also be performed. Continuous administration may be applied where appropriate; for example, where a tumor is excised and the tumor bed is treated to eliminate residual disease. Delivery via syringe or catheterization is preferred. Such continuous perfusion may take place for a period from about 1-6 hours, to about 6-12 hours, to about 12-24 hours, to about 1-2 days, to about 1-2 weeks or longer following the initiation of treatment. Generally, the dose of the therapeutic composition via continuous perfusion will be equivalent to that given by a single or multiple injections, adjusted over a period of time during which the perfusion occurs.

The therapeutic agents are administered to a subject, such as a human patient, in a formulation and in an amount effective to achieve a clinically desirable result. For the treatment of cancer, desirable results include reduction in tumor mass (as determined by palpation or imaging; e.g., by radiography, radionucleotide scan, CAT scan, or MRI), reduction in the rate of tumor growth, reduction in the rate of metastasis formation (as determined e.g., by histochemical analysis of biopsy specimens), reduction in biochemical markers (including general markers such as ESR, and tumor specific markers such as serum PSA), and improvement in quality of life (as determined by clinical assessment, e.g., Karnofsky score), increased time to progression, disease-free survival and overall survival.

The amount of each agent per dose and the number of doses required to achieve such effects will vary depending on many factors including the disease indication, characteristics of the patient being treated and the mode of administration. Typically, the formulation and route of administration will provide a local concentration at the disease site of between 1 nM and 100 µM of each agent, and where the EGF pathway inhibitor is an EGF receptor antibody, a serum concentration of between about 25-500 micrograms/ml. The physician will be able to vary the amount of the compounds, the carrier, the dosing frequency, and the like, taking into consideration such factors as the particular neoplastic disease state and its severity; the overall condition of the patient; the patient's age, sex, and weight; the mode of administration; the suitability of concurrently administering systemic anti-toxicity agents; monitoring of the patient's vital organ functions; and other factors typically monitored during cancer chemotherapy. In general, the compounds are administered at a concentration that affords effective results without causing excessive harmful or deleterious side effects.

In accordance with the invention, the amount of the anti-EGF pathway inhibitor used in combination with a telomerase inhibitor may be less than would be required for the agent used in non-combination therapy.

C. Formulations

The pharmaceutical carrier(s) employed may be solid or liquid. Liquid carriers can be used in the preparation of solutions, emulsions, suspensions and pressurized compositions. The compounds are dissolved or suspended in a pharmaceutically acceptable liquid excipient. Suitable examples of liquid carriers for parenteral administration include water (which may contain additives, e.g., cellulose derivatives, preferably sodium carboxymethyl cellulose solution), phosphate buffered saline solution (PBS), alcohols (including monohydric alcohols and polyhydric alcohols, e.g., glycols) and their derivatives, and oils (e.g., fractionated coconut oil and arachis oil). The liquid carrier can contain other suitable pharmaceutical additives including, but not limited to, the following: solubilizers, suspending agents, emulsifiers, buffers, thickening agents, colors, viscosity regulators, preservatives, stabilizers and osmolarity regulators.

For parenteral administration, the carrier can also be an oily ester such as ethyl oleate and isopropyl myristate. Sterile carriers are useful in sterile liquid form compositions for parenteral administration. Sterile liquid pharmaceutical compositions, solutions or suspensions can be utilized by, for example, intraperitoneal injection, subcutaneous injection, intravenously, or topically. The compositions can also be administered intravascularly or via a vascular stent.

The liquid carrier for pressurized compositions can be a halogenated hydrocarbon or other pharmaceutically acceptable propellant. Such pressurized compositions may also be lipid encapsulated for delivery via inhalation. For administration by intranasal or intrabronchial inhalation or insufflation, the compositions may be formulated into an aqueous or partially aqueous solution, which can then be utilized in the form of an aerosol.

The compositions may be administered topically as a solution, cream, or lotion, by formulation with pharmaceutically acceptable vehicles containing the active compound. The compositions of this invention may be orally administered in any acceptable dosage including, but not limited to, formulations in capsules, tablets, powders or granules, and as suspensions or solutions in water or non-aqueous media. Pharmaceutical compositions and/or formulations comprising the oligonucleotides of the present invention may include carriers, lubricants, diluents, thickeners, flavoring agents, emulsifiers, dispersing aids or binders. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Modes of administration and formulation may be dependent on the drug and its approved mode of administration. For example, when the chemotherapeutic agent is an ant-EGF antibody, IV infusion is indicated, whereas oral administration may be indicated for a small-molecule EGF pathway inhibitor. When the telomerase inhibitor is GRN163L, formulation in 0.9% sodium chloride (normal saline) and administration by i.v. is a preferred route, preferably via infusion over 4-8 hours, e.g. a 6 hr infusion. While the lipid-conjugated oligonucleotides described herein, such as GRN163L, have superior characteristics for cellular and tissue penetration, these and other compounds may be formulated to provide further benefit in this area, e.g. in liposome carriers. The use of liposomes to facilitate cellular uptake is described, for example, in U.S. Pat. Nos. 4,897,355 and 4,394,448, and numerous publications describe the formulation and preparation of liposomes. Liposomal formulations can also be engineered, by attachment of targeting ligands to the liposomal surface, to target sites of neovascularization, such as tumor angiogenic regions. The compounds can also be formulated with additional penetration/transport enhancers, such as unconjugated forms of the lipid moieties described above, including fatty acids and their derivatives. Examples include oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arichidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.). Other useful adjuvants include substrates for transendothelial migration, such as glucose uptake systems for facilitated egress from the vascular space to the tumor microenvironment.

V. Measurement of Telomere Length, Telomerase Activity, and/or Cell Proliferation When employing a therapeutic regimen that involves administration of a telomerase inhibitor, it may be useful to determine telomere length and/or telomerase activity in a cell or tissue sample. These parameters can be measured by assays known in the art. Telomere length can be measured by a flow cytometry method using fluorescence in situ hybridization, referred to as flow FISH (see e.g. M. Hultdin et al., *Nucleic Acids Res.* 26 (16):3651-6, 1998; N. Rufer et al., *Nature Biotechnology* 16:743-7, 1998). Other methods include terminal restriction fragment (TRF) analysis, in which genomic DNA is digested with a restriction enzyme having a four-base recognition sequence not present in telomere repeat sequences, and the restriction fragments are separated according to size, e.g. by gel electrophoresis. See, for example, U.S. Pat. No. 5,489,508 (West et al.) and Harley et al., Nature 345:458, 1990. The West et al. patent also describes methods of measuring telomere length by a "anchored terminal primer" method and by a modified Maxam-Gilbert reaction.

In addition, a more rapid response to a telomerase inhibiting agent may be predicted for tumor cells having shorter telomeric DNA, although telomerase has been shown to have other inhibitory effects independent of telomere length. (e.g. Stewart et al., PNAS 99:12606, 2002; Zhu et al., PNAS 93:6091, 1996; Rubaiyat et al., Oncogene 24 (8):1320, 2005); and Folini et al., Curr. Pharm. Design 11 (9):1105, 2005).

The TRAP assay (see Experimental, below) is a standard method for measuring telomerase activity in a cell extract system (Kim et al., Science 266:2011, 1997; Weinrich et al., Nature Genetics 17:498, 1997). Briefly, this assay measures the amount of nucleotides incorporated into elongation products (polynucleotides) formed by nucleotide addition to a labeled telomerase substrate or primer. The TRAP assay is described in detail in U.S. Pat. Nos. 5,629,154, 5,837,453 and 5,863,726, and its use in testing the activity of telomerase inhibitory compounds is described in various publications, including WO 01/18015. In addition, the following kits are available commercially for research purposes for measuring telomerase activity: TRAPeze™ XK Telomerase Detection Kit (Intergen Co., Purchase N.Y.); and TeloTAGGG Telomerase PCR ELISA plus (Roche Diagnostics, Indianapolis Ind.).

The anticancer activity of the therapeutic combinations can be evaluated using standard in vitro and in vivo assays. The ability of a composition to specifically inhibit the growth of tumor cells can be assayed using tumor cell lines in vitro, or in xenograft animal models in vivo. A preferred protocol for such growth curve assays is the short term cell viability assay described in Asai et al. (2003, cited above). In established xenograft models of human tumors, the test compound is administered either directly to the tumor site or systemically, and the growth of the tumor is followed by physical measurement. A preferred example of a suitable in vivo tumor xenograft assay is also described in Asai et al. (2003, cited above). Other examples are described in Scorski et al., Proc. Natl. Acad. Sci. USA, 94: 3966-3971 (1997) and Damm et al., EMBO J., 20:6958-6968 (2001).

EXPERIMENTAL

A. Preparation and Lipid Conjugation of Oligonucleotide N3'→P5' Phosphoramidates or N3'→P5' Thiophosphoramidates These compounds may be prepared as described, for example, in McCurdy et al., Tetrahedron Letters 38:207-210 (1997) or Pongracz & Gryaznov, Tetrahedron Letters 49:7661-7664 (1999). The starting 3'-amino nucleoside monomers may be prepared as described in Nelson et al., J. Org. Chem. 62:7278-7287 (1997) or by the methods described in Gryaznov et al., US Appn. Pubn. No. 2006/0009636.

A variety of synthetic approaches can be used to conjugate a lipid moiety L to the oligonucleotide, depending on the nature of the linkage selected; see, for example, Mishra et al., Biochim. et Biophys. Acta 1264:229-237 (1995), Shea et al., Nucleic Acids Res. 18:3777-3783 (1995), or Rump et al., Bioconj. Chem. 9:341-349 (1995). Typically, conjugation is achieved through the use of a suitable functional groups at an oligonucleotide terminus. For example, the 3'-amino group present at the 3'-terminus of the NP and NPS oligonucleotides can be reacted with carboxylic acids, acid chlorides, anhydrides and active esters, using suitable coupling catalysts, to form an amide linkage. Thiol groups are also suitable as functional groups (see Kupihar et al., Bioorg. Med. Chem. 9:1241-1247 (2001)). Various amino- and thiol-functionalized modifiers of different chain lengths are commercially available for oligonucleotide synthesis.

Specific approaches for attaching lipid groups to a terminus of an NP or NPS oligonucleotide include those described in US Appn. Pubn. No. 2005/0113325, which is incorporated herein by reference. In addition to the amide linkages noted above, for example, lipids may also be attached to the oligonucleotide chain using a phosphoramidite derivative of the lipid, to produce a phosphoramidate or thiophosphoramidate linkage connecting the lipid and the oligonucleotide. The free 3'-amino group of the fully protected support-bound oligonucleotide may also be reacted with a suitable lipid aldehyde, followed by reduction with sodium cyanoborohydride, which produces an amine linkage.

For attachment of a lipid to the 5' terminus, as also described in US Appn. Pubn. No. 2005/0113325, the oligonucleotide can be synthesized using a modified, lipid-containing solid support. Reaction of 3-amino-1,2-propanediol with a fatty acyl chloride (RC(O)Cl), followed by dimethoxytritylation of the primary alcohol and succinylation of the secondary alcohol, provides an intermediate which is then coupled, via the free succinyl carboxyl group, to the solid support. An example of a modified support is shown below, where S— represents a long chain alkyl amine CPG support, and R represents a lipid.

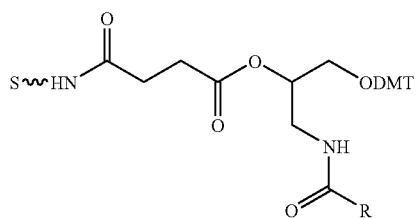

This procedure is followed by synthesis of the oligonucleotide in the 5' to 3' direction, as described, for example, in Pongracz & Gryaznov (1999), starting with deprotection and phosphitylation of the —ODMT group. This is effective to produce, for example, the following structure, after cleavage from the solid support:

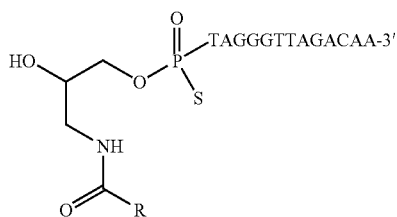

The structure above, when —R is —$(CH_2)_{14}CH_3$ (palmitoyl), is designated herein as GRN163L.

B. FlashPlate™ Assay

This assay was carried out essentially as described in Asai et al., Cancer Research, 63:3931 3939 (2003). Briefly, the assay detects and/or measures telomerase activity by measuring the addition of TTAGGG telomeric repeats to a biotinylated telomerase substrate primer. The biotinylated products are captured on streptavidin-coated microtiter plates, and an oligonucleotide probe complementary to 3.5 telomere repeats, labeled with 33P, is used for measuring telomerase products. Unbound probe is removed by washing, and the amount of probe annealing to the captured telomerase products is determined by scintillation counting.

C. TRAP Assay

The ability of a compound to increase or inhibit telomerase activity in a cell can be determined using the TRAP (Telomeric Repeat Amplification Protocol) assay, which, is described, for example, in Kim et al., U.S. Pat. No. 5,629,154; Harley et al., U.S. Pat. No. 5,891,639; and Harley et al., PCT Pubn. No. WO 2005/000245. Briefly, telomerase-expressing tumor cell lines are incubated with test compositions, lysed, and treated with a labeled oligonucleotide telomerase substrate, appropriate primers, and internal standard for quantitation purposes. Depending on the telomerase activity of the medium, telomere repeats will be added to the substrate, to form telomerase extended products. The mixture is incubated at room temperature, followed by multiple cycles of PCR. The mixture is separated on a gel, and labeled extension product is detected and quantitated via comparison with the internal standard.

D. In Vivo Antitumor Assay Employing GRN163L in Combination with Trastuzumab.

A549 non-small-cell carcinoma cells (approx. $10^7$; TRF length ~4.98 Kb) were implanted subcutaneously into athymic nude mice one day after irradiation. Treatment was initiated when tumors reached ~100 $mm^3$. Groups of twelve mice each were treated in accordance with one of three protocols: (1) GRN163L alone, three times per week (tiw) at 15 mg/kg for four weeks, administered IP; (2) Herceptin alone, at 2.0 mg/kg per mouse for three weeks (4 doses), administered IV; and (3) these treatments in combination (see FIG. 3). The days when Herceptin was administered are indicated with arrows in FIG. 3. A fourth group received saline buffer alone as a control. The results are discussed above.

Although the invention has been described with respect to particular embodiments and applications, those skilled in the art will appreciate the range of applications and methods of the invention disclosed herein.

It is claimed:

1. A method for inhibiting the proliferation of carcinoma cells that express an EGF receptor, comprising
   (a) exposing the cells to an anti-EGF receptor antibody trastuzumab, and
   (b) either preceding, following, or concomitantly with step (a), exposing the cells to a telomerase inhibitor comprising an oligonucleotide which is characterized by:
      (i) N3'→P5' thiophosphoramidate internucleoside linkages;
      (ii) comprising the sequence identified as SEQ ID NO: 12; and
      (iii) a palmitoyl (C16) moiety linked to the 5' terminus of the oligonucleotide via a glycerol or aminoglycerol linker
   wherein the carcinoma cells are breast cancer or non-small cell lung cancer cells.

2. The method of claim 1, wherein the oligonucleotide is 13-20 bases in length.

3. The method of claim 2 wherein the telomerase inhibitor is the compound designated herein as GRN163L.

4. The method of claim 1, for use in treating a subject having carcinoma, wherein exposing step (a) includes administering the anti-EGF receptor antibody to the subject in an amount effective, when the antibody is administered alone, to inhibit proliferation of the carcinoma cells in the subject.

5. The method of claim 4, for use in treating a subject having breast cancer characterized by overexpression of HER2 in the carcinoma cells, wherein the exposing step (a) includes administering the anti-EGF receptor antibody to the subject in an amount effective, when the antibody is administered alone, to inhibit proliferation of the carcinoma cells in the subject.

6. The method of claim 4, wherein each exposing step (a) and (b) includes administering the respective antibody and inhibitor to the subject in an amount effective, when each compound is administered alone, to inhibit proliferation of cancer cells in the subject.

7. The method of claim 4, wherein the telomerase inhibitor is the compound GRN163L, and step (b) includes infusing the telomerase inhibitor intravenously into the subject, under infusion conditions effective to produce a blood concentration of the telomerase inhibitor of between 1 nM and 100 µM.

8. A method for enhancing the treatment efficacy of an anti-EGF receptor antibody trastuzumab in a subject with a carcinoma that express an EGF receptor, comprising
administering to the subject, before, during, or after administering the anti-EGF receptor antibody trastuzumab, an oligonucleotide telomerase inhibitor wherein the oligonucleotide telomerase inhibitor is characterized by:
(i) N3'→P5' thiophosphoramidate internucleoside linkages;
(ii) having the sequence identified as SEQ ID NO: 12; and
(iii) a palmitoyl (C16) moiety linked to the 5' terminus of the oligonucleotide via a glycerol or aminoglycerol linker
wherein the carcinoma is breast cancer or non-small cell lung cancer.

9. The method of claim 8, wherein the telomerase inhibitor is administered in an amount effective to inhibit the proliferation of carcinoma cells in the subject, when the telomerase inhibitor is administered alone.

10. The method of claim 8, wherein enhanced treatment efficacy is evidenced by an increased survival time of the subject, inhibition of tumor growth in the subject, or a combination thereof.

11. The method of claim 8, wherein the oligonucleotide telomerase inhibitor is GRN163L.

12. The method of claim 11, wherein said administering includes infusing the oligonucleotide telomerase inhibitor intravenously into the subject, under infusion conditions effective to produce a blood concentration of the inhibitor of between 1 nM and 100 µM.

* * * * *

SEQUENCE LISTING

```
<160> NUMBER OF SEQ ID NOS: 27

<210> SEQ ID NO 1
<211> LENGTH: 554
<212> TYPE: RNA
<213> ORGANISM: Homo sapiens

<400> SEQUENCE: 1
ggguugcgga gguggggccu gggaggggug guggccauuu uuugcuaac ccuaacugag      60 aagggcguag gcgccgugcu uuugcucccc gcgcgcuguu uuucucgcug acuuucagcg    120
ggcggaaaag ccucggccug ccgccuucca ccguucauuc uagagcaaac aaaaaauguc    180
agcugcuggc ccguucgccu cccggggacc ugcggcgggu cgccugccca gccccgaac     240 cccgccugga gccgcggucg gcccggggcu ucuccggagg cacccacugc caccgcgaag    300
aguugggcuc ugucagccgc gggucucucg ggggcgaggg cgagguucac cguuucaggc    360
cgcaggaaga ggaacggagc gagucccgcc gcggcgcgau ucccugagcu gugggacgug    420
cacccaggac ucggcucaca caugcaguuc gcuuccugu ugguggggg aacgccgauc      480 gugcgcaucc gucaccccuc gccggcagug ggggcuugug aacccccaaa ccugacugac    540
ugggccagug ugcu                                                     554

<210> SEQ ID NO 2
<211> LENGTH: 20
<212> TYPE: DNA
<213> ORGANISM: Artificial Sequence
<220> FEATURE:
<223> OTHER INFORMATION: Oligonucleoide

<400> SEQUENCE: 2
acattttttg tttgctctag                                                20

<210> SEQ ID NO 3
<211> LENGTH: 30
<212> TYPE: DNA
<213> ORGANISM: Artificial Sequence
```

-continued

```
<220> FEATURE:
<223> OTHER INFORMATION: Oligonucleoide

<400> SEQUENCE: 3
gctctagaat gaacggtgga aggcggcagg                                    30

<210> SEQ ID NO 4
<211> LENGTH: 14
<212> TYPE: DNA
<213> ORGANISM: Artificial Sequence
<220> FEATURE:
<223> OTHER INFORMATION: Oligonucleoide

<400> SEQUENCE: 4
gtggaggcgg cagg                                                     14

<210> SEQ ID NO 5
<211> LENGTH: 13
<212> TYPE: DNA
<213> ORGANISM: Artificial Sequence
<220> FEATURE:
<223> OTHER INFORMATION: Oligonucleoide

<400> SEQUENCE: 5
ggaaggcggc agg                                                      13

<210> SEQ ID NO 6
<211> LENGTH: 13
<212> TYPE: DNA
<213> ORGANISM: Artificial Sequence
<220> FEATURE:
<223> OTHER INFORMATION: Oligonucleoide

<400> SEQUENCE: 6
gtggaaggcg gca                                                      13

<210> SEQ ID NO 7
<211> LENGTH: 11
<212> TYPE: DNA
<213> ORGANISM: Artificial Sequence
<220> FEATURE:
<223> OTHER INFORMATION: Oligonucleoide

<400> SEQUENCE: 7
gtggaaggcg g                                                        11

<210> SEQ ID NO 8
<211> LENGTH: 13
<212> TYPE: DNA
<213> ORGANISM: Artificial Sequence
<220> FEATURE:
<223> OTHER INFORMATION: Oligonucleoide

<400> SEQUENCE: 8
cggtggaagg cgg                                                      13

<210> SEQ ID NO 9
<211> LENGTH: 13
<212> TYPE: DNA
<213> ORGANISM: Artificial Sequence
<220> FEATURE:
<223> OTHER INFORMATION: Oligonucleoide

<400> SEQUENCE: 9
acggtggaag gcg                                                      13
```

-continued

<210> SEQ ID NO 10
<211> LENGTH: 16
<212> TYPE: DNA
<213> ORGANISM: Artificial Sequence
<220> FEATURE:
<223> OTHER INFORMATION: Oligonucleoide

<400> SEQUENCE: 10
aacggtggaa ggcggc    16

<210> SEQ ID NO 11
<211> LENGTH: 18
<212> TYPE: DNA
<213> ORGANISM: Artificial Sequence
<220> FEATURE:
<223> OTHER INFORMATION: Oligonucleoide

<400> SEQUENCE: 11
atgaacggtg gaaggcgg    18

<210> SEQ ID NO 12
<211> LENGTH: 13
<212> TYPE: DNA
<213> ORGANISM: Artificial Sequence
<220> FEATURE:
<223> OTHER INFORMATION: Oligonucleoide

<400> SEQUENCE: 12
tagggttaga caa    13

<210> SEQ ID NO 13
<211> LENGTH: 13
<212> TYPE: DNA
<213> ORGANISM: Artificial Sequence
<220> FEATURE:
<223> OTHER INFORMATION: Oligonucleoide

<400> SEQUENCE: 13
cagttagggt tag    13

<210> SEQ ID NO 14
<211> LENGTH: 12
<212> TYPE: DNA
<213> ORGANISM: Artificial Sequence
<220> FEATURE:
<223> OTHER INFORMATION: Oligonucleoide

<400> SEQUENCE: 14
tagggttaga ca    12

<210> SEQ ID NO 15
<211> LENGTH: 11
<212> TYPE: DNA
<213> ORGANISM: Artificial Sequence
<220> FEATURE:
<223> OTHER INFORMATION: Oligonucleoide

<400> SEQUENCE: 15
tagggttaga c    11

<210> SEQ ID NO 16
<211> LENGTH: 11
<212> TYPE: DNA
<213> ORGANISM: Artificial Sequence
<220> FEATURE:
<223> OTHER INFORMATION: Oligonucleoide

```
<400> SEQUENCE: 16
gttagggtta g                                                             11

<210> SEQ ID NO 17
<211> LENGTH: 13
<212> TYPE: DNA
<213> ORGANISM: Artificial Sequence
<220> FEATURE:
<223> OTHER INFORMATION: Oligonucleoide

<400> SEQUENCE: 17
gttagggtta gac                                                           13

<210> SEQ ID NO 18
<211> LENGTH: 15
<212> TYPE: DNA
<213> ORGANISM: Artificial Sequence
<220> FEATURE:
<223> OTHER INFORMATION: Oligonucleoide

<400> SEQUENCE: 18
gttagggtta gacaa                                                         15

<210> SEQ ID NO 19
<211> LENGTH: 9
<212> TYPE: DNA
<213> ORGANISM: Artificial Sequence
<220> FEATURE:
<223> OTHER INFORMATION: Oligonucleoide

<400> SEQUENCE: 19 gggttagac                                                                 9

<210> SEQ ID NO 20
<211> LENGTH: 9
<212> TYPE: DNA
<213> ORGANISM: Artificial Sequence
<220> FEATURE:
<223> OTHER INFORMATION: Oligonucleoide

<400> SEQUENCE: 20 cagttaggg                                                                 9

<210> SEQ ID NO 21
<211> LENGTH: 12
<212> TYPE: DNA
<213> ORGANISM: Artificial Sequence
<220> FEATURE:
<223> OTHER INFORMATION: Oligonucleoide

<400> SEQUENCE: 21
cccttctcag tt                                                            12

<210> SEQ ID NO 22
<211> LENGTH: 12
<212> TYPE: DNA
<213> ORGANISM: Artificial Sequence
<220> FEATURE:
<223> OTHER INFORMATION: Oligonucleoide

<400> SEQUENCE: 22
cgcccttctc ag                                                            12
```

```
<210> SEQ ID NO 23
<211> LENGTH: 13
<212> TYPE: DNA
<213> ORGANISM: Artificial Sequence
<220> FEATURE:
<223> OTHER INFORMATION: Oligonucleoide

<400> SEQUENCE: 23
taggtgtaag caa                                                         13

<210> SEQ ID NO 24
<211> LENGTH: 13
<212> TYPE: DNA
<213> ORGANISM: Artificial Sequence
<220> FEATURE:
<223> OTHER INFORMATION: Oligonucleoide

<400> SEQUENCE: 24
ttgtctaacc cta                                                         13

<210> SEQ ID NO 25
<211> LENGTH: 11
<212> TYPE: DNA
<213> ORGANISM: Artificial Sequence
<220> FEATURE:
<223> OTHER INFORMATION: Oligonucleoide

<400> SEQUENCE: 25
gttgagtgta g                                                           11

<210> SEQ ID NO 26
<211> LENGTH: 6
<212> TYPE: DNA
<213> ORGANISM: Artificial Sequence
<220> FEATURE:
<223> OTHER INFORMATION: Oligonucleoide

<400> SEQUENCE: 26 ttaggg                                                                  6

<210> SEQ ID NO 27
<211> LENGTH: 10
<212> TYPE: DNA
<213> ORGANISM: Artificial Sequence
<220> FEATURE:
<223> OTHER INFORMATION: Oligonucleoide

<400> SEQUENCE: 27
tttttttttt                                                             10
```